US012453613B2

(12) United States Patent
Thomas et al.

(10) Patent No.: US 12,453,613 B2
(45) **Date of Patent: *Oct. 28, 2025**

(54) CONTAINER CLOSURE

(71) Applicant: Aesculap AG, Tuttlingen (DE)

(72) Inventors: Stefan Thomas, Tuttlingen (DE); Andreas Elisch, Dunningen (DE); Karl-Heinz Eiskant, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/744,925

(22) Filed: Jun. 17, 2024

(65) Prior Publication Data

US 2024/0335248 A1 Oct. 10, 2024

Related U.S. Application Data

(63) Continuation of application No. 17/256,926, filed as application No. PCT/EP2019/068706 on Jul. 11, 2019, now Pat. No. 12,048,568.

(30) Foreign Application Priority Data

Jul. 13, 2018 (DE) .................... 10 2018 117 046.7

(51) Int. Cl.
*A61B 50/30* (2016.01)
*B65D 45/24* (2006.01)
*A61B 50/00* (2016.01)

(52) U.S. Cl.
CPC .............. *A61B 50/30* (2016.02); *B65D 45/24* (2013.01); *A61B 2050/0061* (2016.02); *A61B 2050/007* (2016.02)

(58) Field of Classification Search
CPC .. A61B 2050/007; A61B 50/30; B65D 45/24; B65D 45/18; B65D 45/22; B65D 45/28;
(Continued)

(56) References Cited

U.S. PATENT DOCUMENTS 5,706,968 A * 1/1998 Riley .................... B65D 45/24 292/145
5,735,428 A 4/1998 Chern
(Continued)

FOREIGN PATENT DOCUMENTS

CN 101342962 A 1/2009
CN 107206116 A 9/2017
(Continued)

OTHER PUBLICATIONS

German Search Report received in Application No. 10 2018 117 046.7 dated Jan. 8, 2019, with translation, 13 pages.
(Continued)

*Primary Examiner* — Robert Poon
(74) *Attorney, Agent, or Firm* — Christopher A. Rothe; CM Law

(57) ABSTRACT

A closing/locking mechanism for a sterile container includes an actuation lever, a tension bow or claw coupled to the actuation lever, and an engagement element forming an undercut and with which the tension bow or claw can be brought into operative engagement to apply a tensile force to the engagement element. The tension bow or claw is mounted for sliding transversely to the tensile force to be applied. A spring is arranged in an operative position relative to the tension bow or claw in such a way that, when a predefined actuation position of the actuation lever and a predefined/predefinable sliding position of the tension bow or claw are reached, in which position the tension bow or claw already reaches behind the engagement element, the spring applies a compressive force to the tension bow or claw in the direction of the tensile force.

32 Claims, 6 Drawing Sheets

Figure 1:
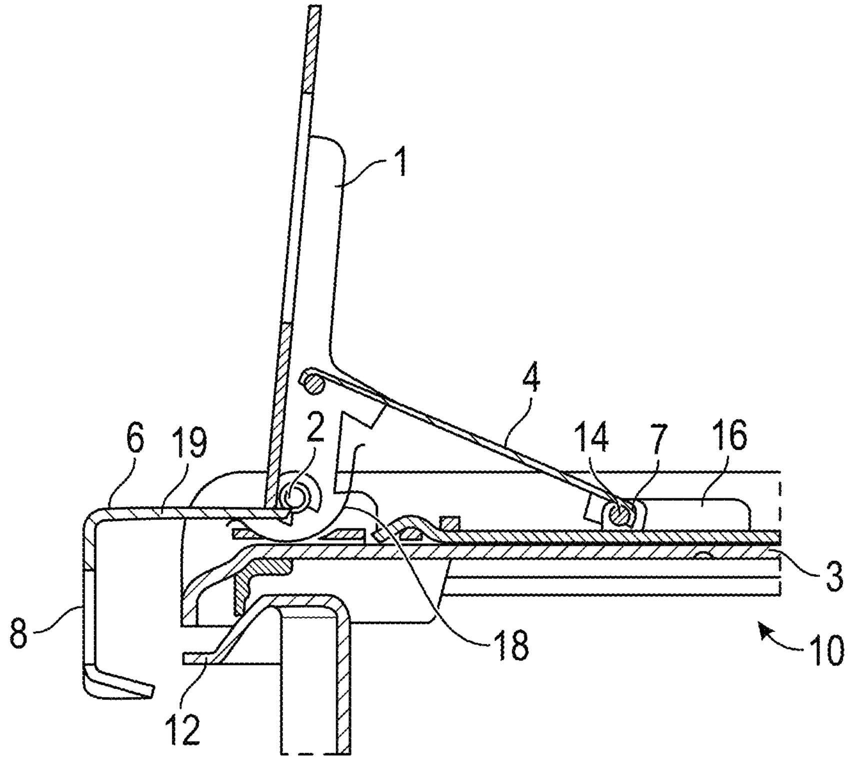

(58) Field of Classification Search
CPC ...... B65D 45/00; B65D 45/02; B65D 45/025; B65D 45/06; B65D 45/08; B65D 45/16; B65D 45/20; B65D 77/2004
USPC .................. 206/363; 220/324, 326, 281, 323
See application file for complete search history.

(56) References Cited

U.S. PATENT DOCUMENTS

| | | | | |
|---|---|---|---|---|
| 6,494,337 | B1 | 12/2002 | Moroni | |
| 8,496,133 | B2 | 7/2013 | Mizukoshi et al. | |
| 12,048,568 | B2 * | 7/2024 | Thomas | A61B 50/30 |
| 2006/0042897 | A1 * | 3/2006 | Sanderson | E05C 3/30 190/120 |
| 2011/0000916 | A1 | 1/2011 | Dane et al. | |
| 2013/0043250 | A1 | 2/2013 | Kreidler et al. | |
| 2017/0360976 | A1 | 12/2017 | Thomas et al. | |

FOREIGN PATENT DOCUMENTS

| | | | |
|---|---|---|---|
| DE | 202012002487 | U1 | 5/2012 |
| DE | 202013002202 | U1 | 4/2013 |
| DE | 202013002232 | U1 | 4/2013 |
| DE | 202012102803 | U1 | 10/2013 |
| FR | 1578189 | A | 8/1969 |
| WO | 2008078169 | A2 | 7/2008 |
| WO | 2020011932 | A1 | 1/2020 |

OTHER PUBLICATIONS

International Search Report Application No. PCT/EP2019/068706, dated Oct. 9, 2019, with translation, 5 pages.
Office Action received in Chinese Application No. 201980046726.X dated Jun. 27, 2023, with translation, 9 pages.
Office Action received in European Application No. 21 201 923.6 dated May 10, 2023, with translation, 8 pages.
Written Opinion received in Application No. PCT/EP2019/068706 mailed Oct. 9, 2019, with translation, 13 pages.

* cited by examiner

CONTAINER CLOSURE

CROSS REFERENCE TO RELATED APPLICATIONS

This application is a continuation of U.S. application Ser. No. 17/256,926, filed on Dec. 29, 2020, which is now, and which is the United States national phase entry of International Application No. PCT/EP2019/068706, filed on Jul. 11, 2019, which is now expired, and which claims the benefit of priority of German Application No. 10 2018 117 046.7, filed Jul. 13, 2018. The contents of U.S. application Ser. No. 17/256,926, International Application No. PCT/EP2019/068706 and German Application No. 10 2018 117 046.7 are incorporated by reference herein in their entireties.

FIELD

The present invention relates to a closure or respectively closing mechanism/locking mechanism for/of a medical sterile container, in particular for locking a lid on a container trough.

BACKGROUND

Sterile containers of the present type are used, among other things, for the sterilization of medical instruments. For this purpose, the sterile container has a receptacle or container trough, into which instruments to be sterilized can be inserted, a container lid for fluid-tight closure of the container, and a closure/closing mechanism (locking mechanism), by means of which the lid can be firmly locked (in a fluid-tight manner) to the container trough.

In addition, the sterile container is usually designed/equipped with a valve mechanism that prevents the internal container pressure from rising above a predetermined/predeterminable value that could damage the container during a sterilization process in an autoclave.

From the prior art, for example according to relevant products of the present applicant, (medical) sterile containers of the type described above are known, which have a container trough, which can be closed by means of a container lid, as well as a closing/locking mechanism by means of which the lid can be locked to the trough in a fluid-tight manner. A valve device is furthermore provided in the container lid, which permits an inflow of ambient gas into the interior of the container via a (sterilizing) filter device and an outflow of container interior gas into the environment, while bypassing the filter device, in order to keep the internal container pressure below a predetermined/predeterminable value with respect to the ambient pressure. Decisive for the correct function of this valve device is the safe and fluid-tight locking of the lid on/at the container trough in order to prevent unintentional leakage into/out of the container at the contact point between trough and lid.

The so-called swing stopper has proven to be a particularly advantageous configuration of such a closing/locking mechanism. This mechanism has an actuation lever, which is pivotably mounted on the lid, for example, and to which a bracket or claw/clamping claw is hinged, which comes into undercut engagement with a bar projecting laterally, for example on the container trough, and thus pulls the container lid against the container trough when the actuation lever is flipped over. Between the lid and the trough, there is a sealing ring which, when the lid is tightened, is squeezed against the trough and the lid and thus seals the contact area between the trough and the lid. This allows to compensate for even small tolerances.

It is important that

- despite the closing mechanism/closure unit, the largest possible area is left free at the front side of the container underside (container trough), for example for marking the container,
- accidental opening of the closing unit is prevented as far as possible,
- even larger manufacturing tolerances can be compensated, and
- a minimum tightening force between lid and trough is guaranteed.

Furthermore, it would be desirable that

- the tensile force does not increase suddenly but continuously as the actuation lever is progressively turned, in particular to avoid damage to the closing mechanism and/or to the seal,
- the closing mechanism can also assume a pressure relief valve function at the same time,
- the actuation lever is located in an easily accessible position, preferably at the top of the container lid, in order to avoid protruding laterally even during the opening/closing process and not to cover the front of the container trough, and
- the closing mechanism is fixed as stable as possible in its open/unlocked end position.

SUMMARY

In view of the preceding description of the prior art, the object of the present invention is to provide a functional closing/locking mechanism (closing unit) for/of a sterile container, preferably of medical type, via which the above-mentioned, desirable properties can be achieved as completely as possible.

The present invention thus relates to a closing/locking mechanism for/of a sterile container with a preferably pivotably mounted actuation lever, a tension bow/clamping yoke or claw/clamping claw which is directly or indirectly coupled to the actuation lever and an engagement element (bar/ledge) forming an undercut with which the tension bow or claw can be brought into operative/active engagement in order to exert a tensile force on the engagement element upon actuation of the actuation lever. According to the invention, the tension bow or claw is displaceably mounted transversely, preferably at a right angle, to the tensile force to be exerted (force vector), wherein a spring is arranged in an operative position relative to the tension bow or claw, such that this spring only applies a compression force to the tension bow or claw in the direction of (substantially parallel to) the tensile force to be exerted when there is a predetermined actuation position of the actuation lever and consequently a predetermined/predeterminable sliding position of the tension bow or claw in which the latter already engages behind the engagement element.

According to this, actuation of the actuation lever only indirectly causes the container lid to be pulled against the container trough by bringing/moving the tension bow/claw, which is for example on the lid side, into an operative position in a first direction of movement with respect to the trough-side engagement element by means of the actuation lever, in which a spring then applies a compression force to the tension bow/claw in a direction preferably substantially transverse to its direction of movement, which is consequently oriented at least partially parallel to the intended direction of tensile force. This basically ensures a spring force-dependent and thus predefined clamping force between lid and trough, which is not dependent on the actuation force on the actuation lever. The handling of the closing mechanism according to the invention is therefore easier compared to the prior art and its closure safety is higher. In addition, it is possible that the lid opens against the force of the spring when a certain excess pressure inside the container with regard to the atmosphere is reached, thus allowing the internal container pressure to escape into the atmosphere.

The preceding invention principle is preferably constructively realizable by the fact that the actuation lever is coupled, via at least one tappet rod (connecting rod) articulated thereon, with the tension bow or claw/clamping claw for a transformation of its pivoting movement into a translational movement of the tension bow or claw/clamping claw. This means that the actuation lever is coupled to the tension bow in the manner of a toggle lever construction.

It is advantageous that the actuation lever is hinged to the container lid (at the top of the container lid) via at least one, preferably two, axially spaced hinge pins, in such a way that the tension bow or claw/clamping claw with respect to the actuation lever extends below the at least one, preferably between the two axially spaced hinge pins. I.e. the tension bow is located between the container lid (top side) and the actuation lever.

It is also advantageous that the actuation lever forms an actuation plate/button or actuation bracket/handle at one free end portion and a push-down lug at its other free end portion, which in the unfolded state of the actuation lever presses down the tension bow or claw/clamping claw with respect to the hinge pin(s) in the direction of the container lid (top side) and in the folded state of the actuation lever releases the tension bow or claw/clamping claw for its movement towards the hinge pin(s) (away from the container lid).

Since the tension bow or claw forms a hook at one of its end portions that surrounds the edge of the container lid and is intended to latch with the trough-side engagement element (bar), the hook engages under the engagement element (bar) substantially without contact when the tension bow/claw is in the pressed-down position and only contacts the engagement element (bar) when the predetermined sliding position is reached.

In order to achieve a spring force, it is advantageous that the spring, preferably as a leaf spring, is placed around the hinge pin(s) or their longitudinal axis in a sickle or part-circular shape, such that it rests at its one free leaf spring edge (spring end portion) against a lower side of the tension bow or claw/clamping claw with respect to the hinge pin(s) and only then presses at its other free leaf spring edge (spring end portion) against a tongue/protrusion/portion of the tension bow or claw/clamping claw extending in the sliding direction of the tension bow or claw/clamping claw, when it reaches the predetermined sliding position to create the compression force on the tension bow or claw/clamping claw at its one free leaf spring edge (spring end portion).

Alternatively, it may be provided that the spring, preferably in the form of a bow/yoke spring, is fixed to the tension bow or claw/clamping claw in such a way that, when the tension bow or claw/clamping claw is displaced it is resiliently supported on the container lid when the tension bow or claw/clamping claw reaches the predetermined sliding position, so as to generate the compression force on the tension bow or claw/clamping claw.

Further alternatively, it may be provided that the spring, preferably in the form of a corrugated or curved leaf spring, is fixed to the container lid in such a way that the tension bow or claw/clamping claw, at least when it reaches the predetermined sliding position, slides over the spring so as to apply the compression force to the tension bow or claw/clamping claw.

BRIEF DESCRIPTION OF THE DRAWING FIGURES

The invention is explained in more detail below on the basis of preferred embodiments with reference to the accompanying Figures.

Figure 2:
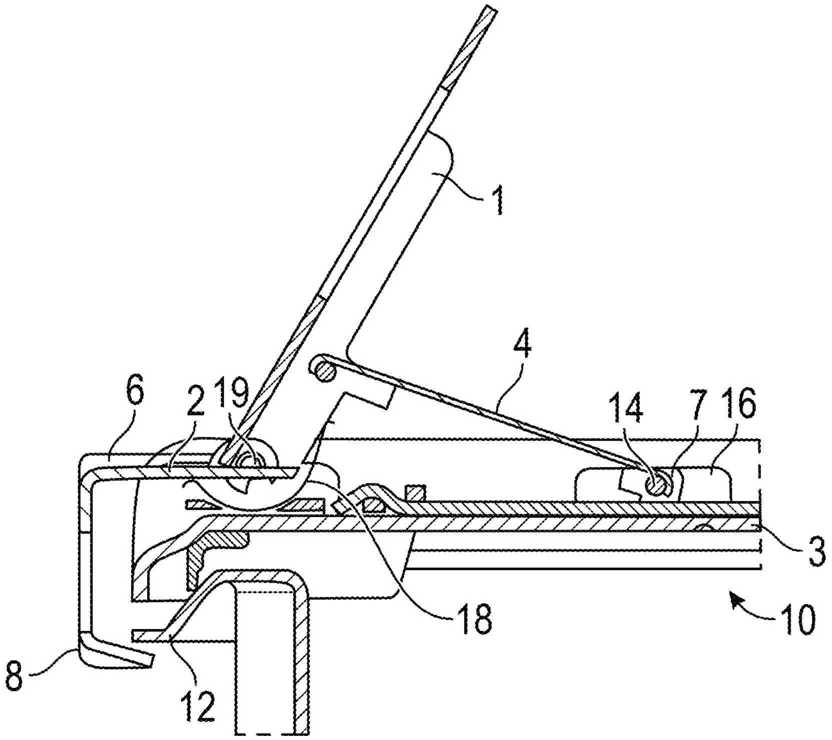
Figure 3:
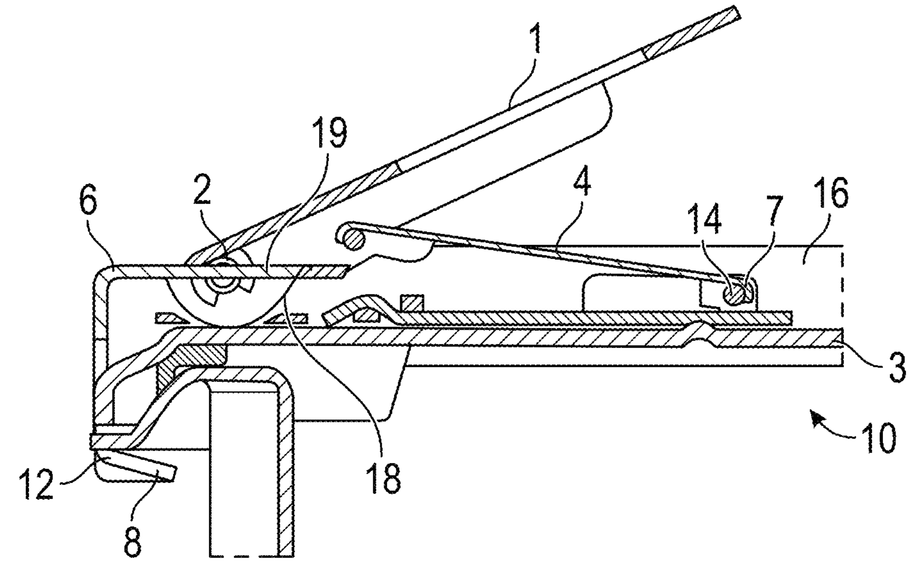
Figure 4:
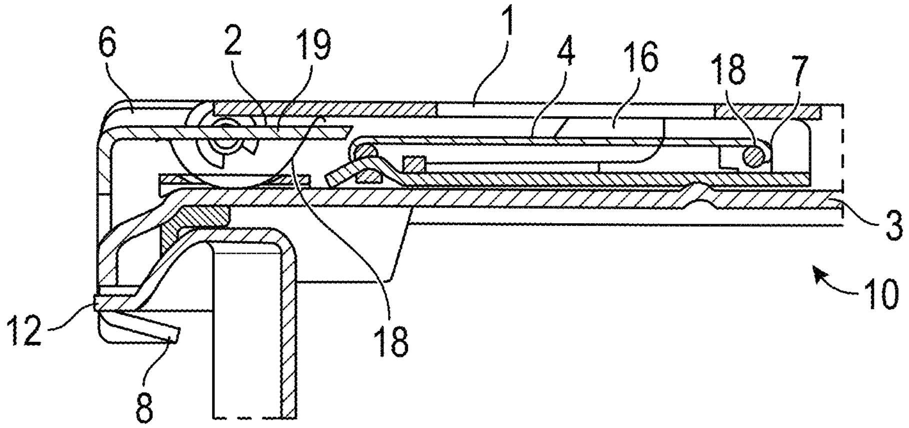
Figure 5:
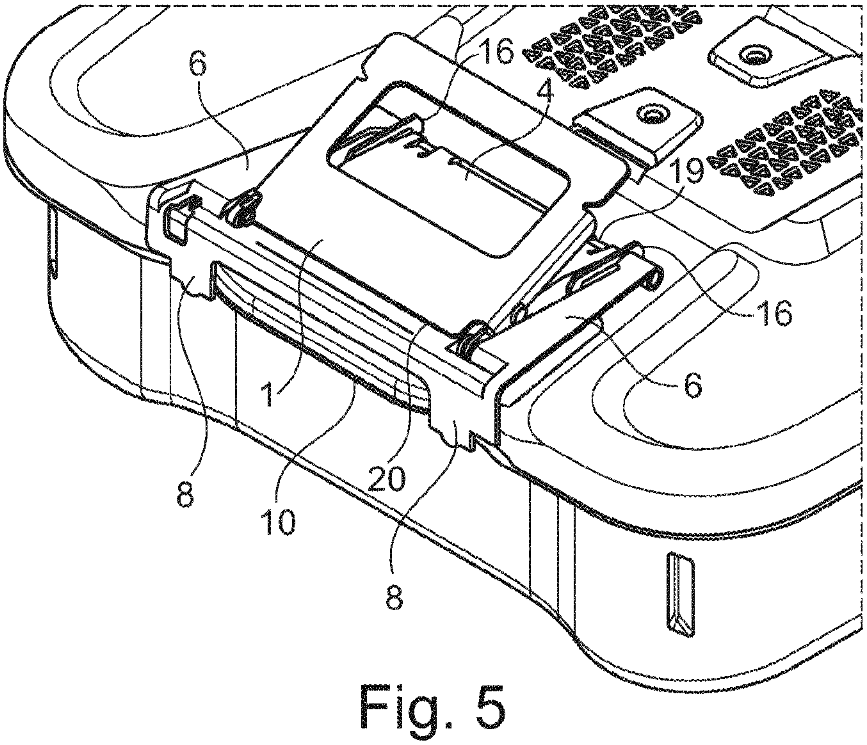
Figure 6:
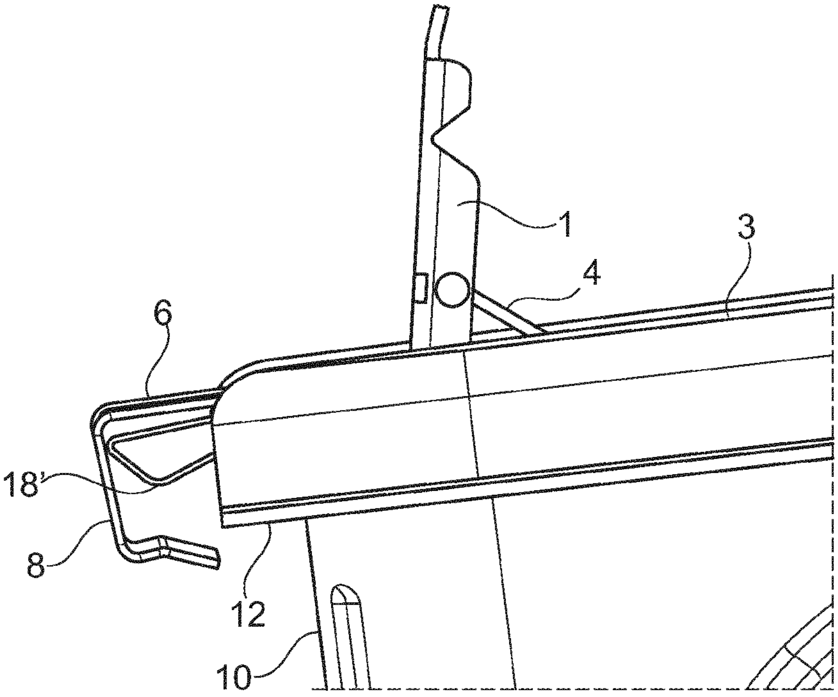

FIG. 1 shows a cross-section of a closing/locking mechanism according to a first preferred embodiment of the invention in a completely unlocked (unclosed) state, FIG. 2 shows the closing/locking mechanism according to the first embodiment at the beginning of a locking process, FIG. 3 shows the closing/locking mechanism according to the first embodiment in the further course of the locking process, FIG. 4 shows the closing/locking mechanism according to the first embodiment at the end of the locking process, FIG. 5 shows a perspective view of the closing/locking mechanism according to the first embodiment mounted on the top side of a container lid, FIG. 6 shows a side view of a closing/locking mechanism according to a second embodiment of the present invention.

Figure 7:
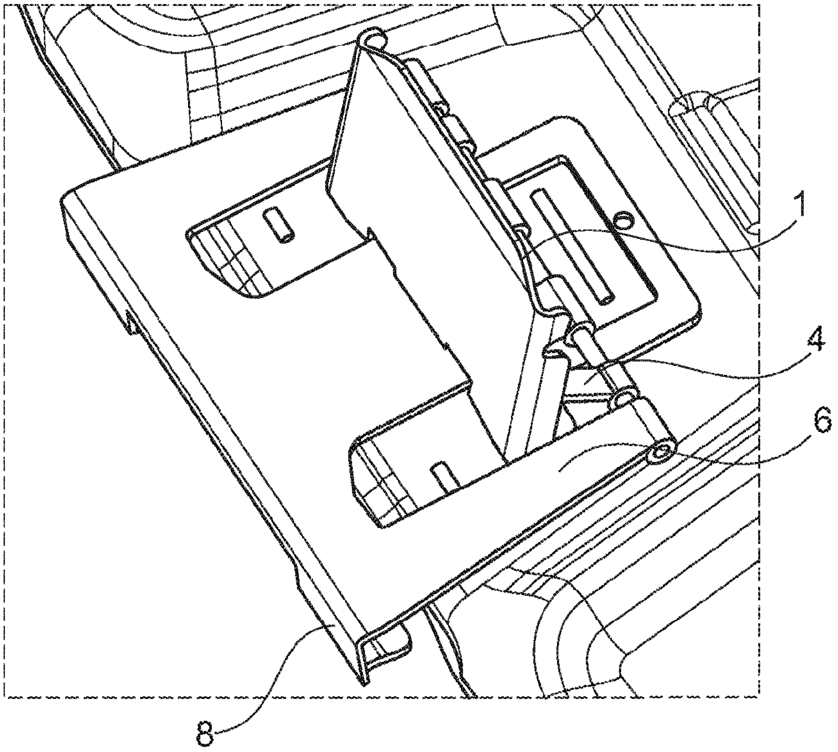
Figure 8:
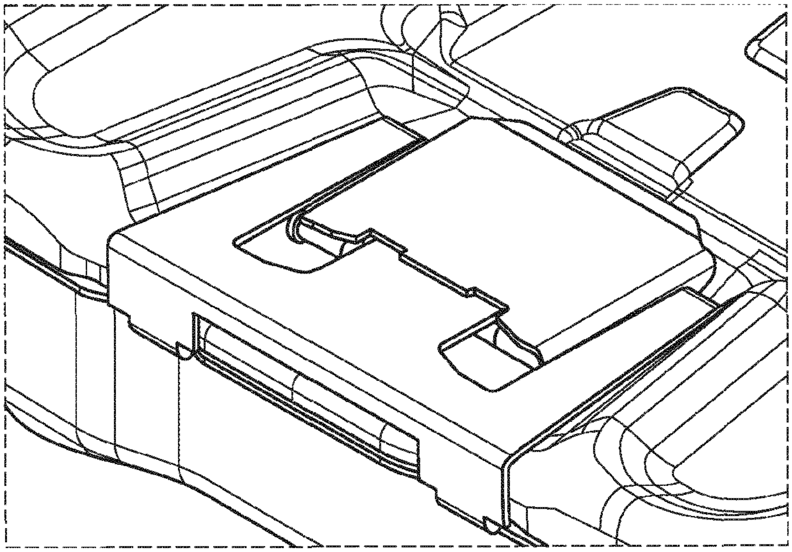
Figure 9:
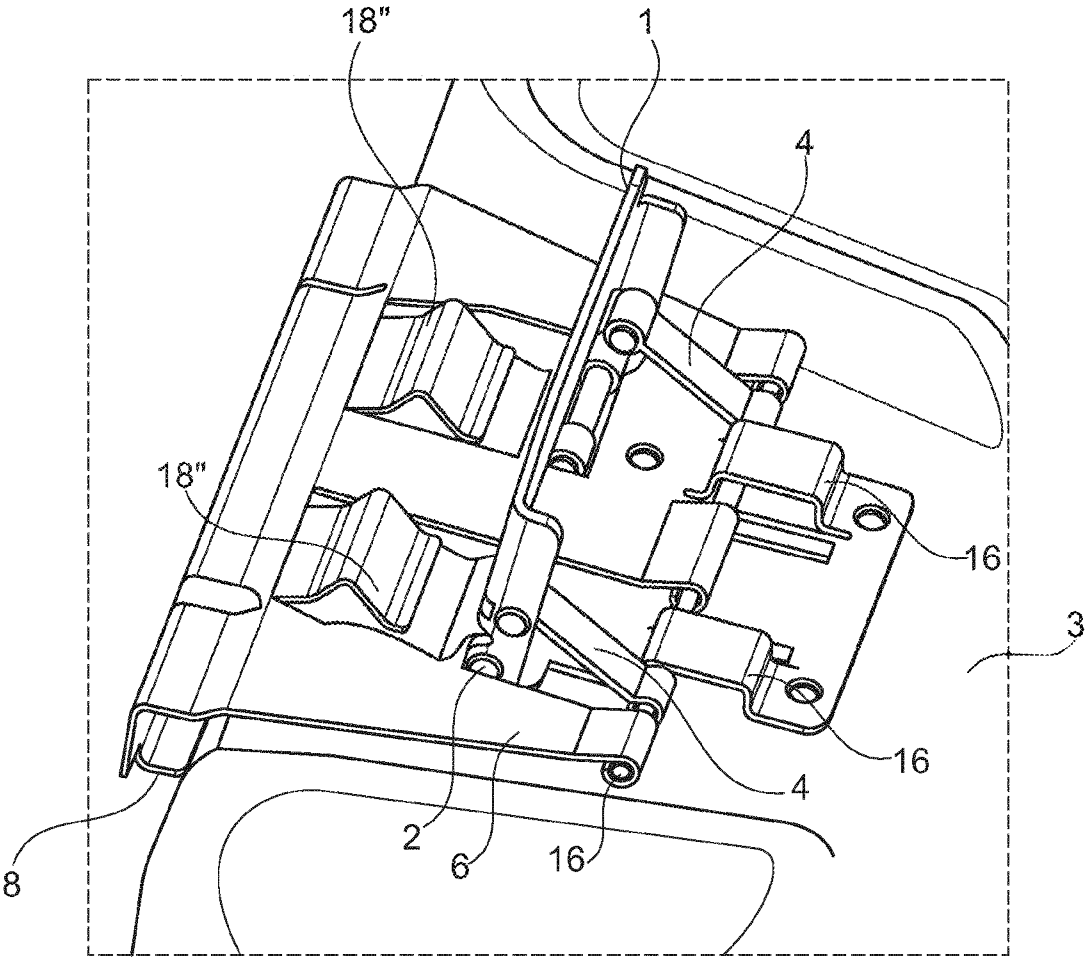
Figure 10:
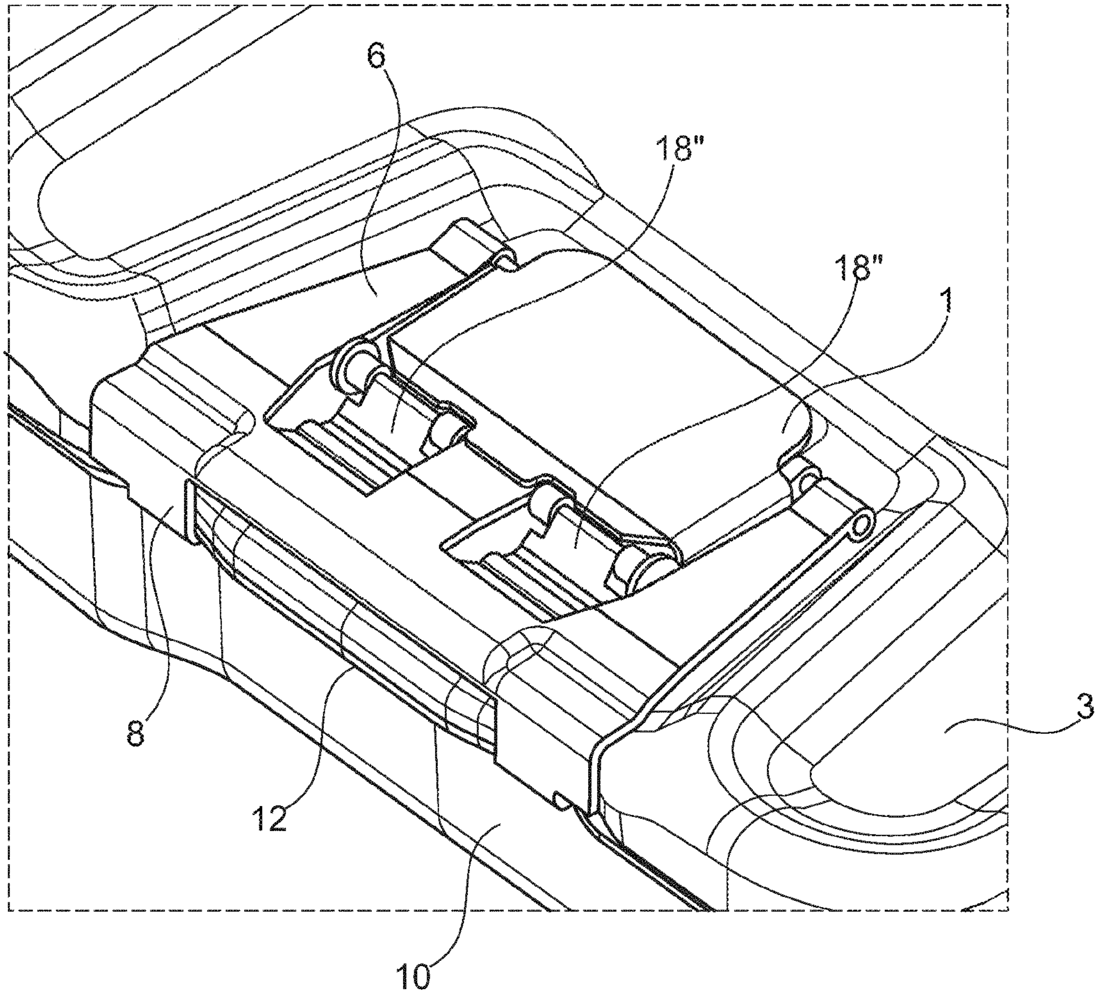

FIG. 7 shows a perspective view of the closing/locking mechanism according to the second embodiment in unlocked (unclosed) state, FIG. 8 shows a perspective view of the closing/locking mechanism according to the second embodiment in locked (unclosed) state, FIG. 9 shows a perspective view of a closing/locking mechanism according to a third embodiment of the present invention in unlocked (unclosed) state, and FIG. 10 shows a perspective view of the closing/locking mechanism according to the third embodiment in a locked (unclosed) state.

DETAILED DESCRIPTION

A locking/closing mechanism according to FIGS. 1 to 5 essentially consists of a preferably flap-shaped or handle-shaped actuation lever 1, which is hinged at/in the area of its one front edge to the top of a container lid 3. Preferably, two axially spaced hinge pins 2 are provided for this purpose, which are inserted through eyelets shown in FIG. 6 only vaguely on the container lid and secured axially. In a central portion of the actuation lever 1, two parallel, spaced tappet rods (connecting rods) or a tappet rod plate 4 (see FIG. 6) is/are hinged at the ends, said tapped rod plate 4 being hinged at its other end to a locking slider 7 on a tension bow 6. The tension bow 6 is mounted on the top of the container lid 3 in a movable manner, so that it can be moved lengthwise depending on the folding position of the actuation lever 1.

At its end opposite the tappet-rod articulation point and projecting freely over the circumferential edge of the container lid 3, the tension bow 6 has/forms a claw/hook or clamping element 8 bent in the direction of the lid underside, which is designed and provided to enter into an undercut operative engagement with a bar/ledge 12 formed on the circumference of a container trough 10, as is particularly well illustrated in FIGS. 3 and 4.

The mounting of the tension bow 6 on the top of the container lid 3 is such that the tension bow 6 can on the one hand be moved in its longitudinal direction and on the other hand can be moved/pivoted upwards at its freely projecting end portion, i.e. away from the upper lid side. In terms of design, this can be achieved, for example, by hinging the tappet rod/tappet rod plate 4 to an eyelet (not shown in more detail) formed on the tension bow 6, by inserting through each eyelet a hinge stud or a continuous hinge rod 14, which in turn is slid in a guide rail 16 on the container lid 3, which may also define a fixed end stop at least for the final unlocking position of the actuation lever 1.

Below and/or between the hinge pins 2 of the actuation lever 1, according to FIG. 1, there is a leaf spring 18 which is arched/bent to form a bow or trough and is therefore located between the upper lid side and the tension bow 6 or the actuation lever 1. The spring 18 is oriented in such a way that its convex bulging center portion (directly or indirectly) rests against the top of the container lid 3, whereas its free end edges extend upwards, i.e. towards the actuation lever 1.

The tension bow 6 further has a preferably tongue-shaped plate portion 19 extending towards the hinge stud/hinge rod 14, which is oriented substantially parallel to the top of the container lid 3 and is provided to slide over the end edges of the spring 18 projecting freely upwards in the locking direction upon actuation of the actuation lever 1, thereby flattening (bending-tensioning) the spring 18 in order to generate a spring compression force towards the underside of the tension bow 6 facing the container lid 3 (i.e. upwards).

Finally, the actuation lever 1 is designed with a push-down lug 20 (see in particular FIG. 5 and FIG. 6) on its one hinged front edge, which extends or protrudes beyond the front edge, so that at least when the actuation lever 1 is fully opened it is positioned underneath the hinge pins 2 (i.e. between the hinge pins 2 and the tension bow 6) and thus pushes the tension bow 6 downwards, i.e. towards the top of container lid 3.

The functioning of the closing/locking mechanism (unit) according to the first preferred embodiment of the present invention can be described as follows:

In the fully unlocked/unclosed state of the closing/locking mechanism as shown in FIG. 1, the actuation lever 1 is oriented almost perpendicular to the top of the container lid 3, causing the tension bow 6 to be pushed far beyond the circumferential edge of the container lid 3 in such a way that its clamping element 8 is positioned away from the trough-side bar 12. At the same time, the plate portion 19 of the tension bow 6 is at a distance from the end edges of the spring 18 projecting freely upwards, so that the spring does not exert any spring force on the tension bow 6. Finally, the tension bow 6 is pushed towards the upper lid side by the push-down lug 20 of the actuation lever 1, so that its clamping element 8 is located far below the bar 12.

As soon as the actuation lever 1 is flipped (manually), this pivoting movement via the tappet rod/tappet rod plate 14 causes a translation/sliding movement of the locking slider 7, whereby the clamping element 8 of the tension bow 6 approaches the trough-side bar 12 parallel to the upper lid side. At the same time, the plate portion 19 of the tension bow 6 approaches the upward-projecting end edges of the spring 18.

When a substantially half-closed/half-locked position is reached as shown in FIGS. 3 and 6, the plate portion 19 slides step by step over the two end edges of the spring 18 in order to flatten them. The resulting spring force pushes the tension bow 6 upwards, i.e. away from the upper lid side, causing the clamping element 8 of the tension bow 6 to contact the underside of the trough-side bar 12 and to increasingly exert a tensile force on it. This causes the container lid 3 to be increasingly pulled against the upper edge of the container trough 10.

In the end position according to FIG. 4, the actuation lever 1 has slightly exceeded the horizontal line through the hinge pins 2 (dead center line) towards the container lid 3 and is thus held in the fully locked position in a self-locking manner.

This means that the actuation force on the actuation lever 1 only has to be large enough to move the tension bow 6 longitudinally while overcoming frictional forces, whereas the actual tightening/closing force between lid 3 and trough 10 is generated by the spring 18. Since the spring 18 is bent trough-like around the hinge pin(s) 2 of the actuation lever 1, it requires only little space and makes the entire closing/locking mechanism compact. Furthermore, since only the clamping element 8 protrudes over the circumferential border of the lid 3 towards the trough 10, the trough front surface is only slightly covered by the closing/locking mechanism, i.e. within the frame of the clamping element 8 even with a large-sized actuation lever 1. Finally, the spring travel achieved by the spring 18, which is considerably greater than that of a conventional elastic seal between lid and trough, allows a kind of pressure relief valve function of the closing/locking mechanism, in that if the spring-dependent value of the internal container pressure is exceeded, the lid 3 is lifted off the trough 10 against the spring pre-tensioning by the spring 18, thus causing a deliberate (large-volume) temporary leakage.

In the following, a second embodiment of the present invention will be described on the basis of FIGS. 6 to 8, wherein substantially only the constructional features different from the first embodiment are discussed. With regard to all other features and functions, it is referred to the preceding figure description.

In the second embodiment, the trough-shaped spring 18 known from the first embodiment is replaced by a bending spring 18' fixed to the tension bow 6 and moving/shifting with it. Specifically, as shown in FIG. 6, a (leaf) spring 18', which is wedge-shaped in side view, is fixed to the underside of the tension bow 6 facing the upper lid side and tapers continuously and/or in steps towards the articulation point of the tappet rod 4 on the tension bow 6. The circumferential edge of the container lid 3 forms a slideway for the spring 18'.

As a result, when the tension bow 6 is moved via the actuation lever 1 to lock the container, the spring 18' slides along the slideway starting from the spring tip towards its wedge-shaped maximum height portion, thus increasing the spring compression force exerted on the tension bow 6 and thus pressing the clamping element 8 against the underside of the bar 12. As a result, the lid 3 is pulled against the trough 10, as already described with the first embodiment.

The second embodiment functionally provides the same advantages as the first embodiment, wherein contrary to this the spring 18' is exposed at least in the unlocked position of the locking/closing mechanism.

In the following, a third embodiment of the present invention will be described on the basis of FIGS. 9 and 10, wherein substantially only the constructional features different from the first and second embodiment are discussed. With regard to all other features and functions, it is referred to the preceding figure description.

As mentioned above, the spring 18' is fixed to the tension bow 6 in order to move together with it. As an alternative, it is also possible to fix a corresponding spring 18" to the container lid 3, as shown in particular in FIG. 9.

In other words, the third embodiment of the present invention provides to form the tension bow 6 with at least one, preferably two window-like cutouts, in the respective areas of which a corrugated or single curved leaf spring 18" is mounted on the container lid 3, such that each spring 18" projects with its respective convexly curved central portion upwards (away from the upper lid side) through the associated window-like cutout when the closing/locking mechanism assumes an unlocked/unclosed position as shown in FIG. 9. In this state, the tension bow 6 is pushed down towards the upper lid side by the push-down lug 20 on the actuation lever 1 without generating an opposing spring force on it.

However, as soon as the actuation lever 1 is swung towards the locking position and the tension bow 6 is moved, the curved leaf springs 18" move out of the window-like cutouts, i.e. the tension bow 6 increasingly slides over the two leaf springs 18", causing them to flatten out and thus apply a compression force to the underside of the tension bow 6. In addition, in this case all advantages of the first embodiment can be realized.

The invention claimed is:

1. A medical sterile container comprising:
- a container trough comprising a sidewall having an upper edge;
- a container lid; and
- a closing/locking mechanism,
- the container lid being arranged on the upper edge of the container trough and lockable with the container trough by the closing/locking mechanism,
- the closing/locking mechanism comprising:
- an actuation lever that is pivotable between a locked position, in which the container lid is locked to the container trough in a fluid-tight manner, and an unlocked position,
- a tension bow directly or indirectly coupled to the actuation lever and displaceable relative to the container lid,
- a spring disposed between a portion of the tension bow and a portion of the container lid; and
- an engagement element forming an undercut on the container trough, wherein
- when the actuation lever is pivoted from the unlocked position to the locked position:
- the tension bow moves upwardly toward the upper edge of the container trough and inwardly toward the sidewall to engage behind the engagement element,
- the tension bow moves over the spring and compresses the spring against said portion of the container lid, and
- the spring applies a force to the tension bow, thereby pressing the container trough against the container lid in said fluid-tight manner.

2. The medical sterile container according to claim 1, further comprising a tappet having a first end coupled to the actuation lever and a second end coupled to the tension bow, the tappet being operable to convert pivot motion of the actuation lever to translation of the tension bow.

3. The medical sterile container according to claim 2, wherein the tappet comprises a tappet rod or a tappet plate.

4. The medical sterile container according to claim 1, wherein the tension bow comprises a first section defining a clamping element and a second section defining a locking slider that moves in unison with the clamping element.

5. The medical sterile container according to claim 4, wherein translation of the locking slider is limited by a guide rail on the container lid.

6. The medical sterile container according to claim 4, wherein the engagement element on the container trough comprises an abutment surface, and wherein, when the actuation lever is pivoted from the unlocked position to the locked position, the clamping element contacts the abutment surface on the container trough, and the spring exerts the force on an underside of the tension bow to pull the clamping element against the abutment surface.

7. The medical sterile container according to claim 6, wherein the abutment surface extends along a perimeter of the container trough.

8. The medical sterile container according to claim 6, wherein the abutment surface forms a ledge that extends outwardly and away from an interior of the container trough.

9. The medical sterile container according to claim 6, wherein the clamping element comprises a hook configured to hook onto the abutment surface.

10. The medical sterile container according to claim 9, wherein the hook projects towards the container trough when the container lid is placed on the container trough.

11. The medical sterile container according to claim 1, wherein the actuation lever comprises a first end that forms an actuation handle and a second end that forms a push-down lug, the push-down lug configured to press against the tension bow when the actuation lever is pivoted toward the unlocked position and release the tension bow when the actuation lever is pivoted toward the locked position.

12. The medical sterile container according to claim 1, wherein the actuation lever is pivotally mounted on a pin, and the spring is bent around the pin.

13. The medical sterile container according to claim 1, wherein the spring is a leaf spring that comprises a first free edge and a second free edge, the first free edge and the second free edge configured to engage the tension bow after the actuation lever is pivoted to the locked position and the tension bow slides over the spring.

14. The medical sterile container according to claim 1, wherein the spring is configured such that, when the container trough and the container lid are pressed against each other in said fluid-tight manner, and when a pressure in the medical sterile container exceeds a certain value, said pressure in the medical sterile container overcomes a reaction force of the spring to separate the container lid from the container trough to relieve excess pressure in the medical sterile container.

15. The medical sterile container according to claim 1, wherein the spring is arranged between an underside of the tension bow and an upper side of the container lid.

16. A medical sterile container comprising:
- a container trough having a sidewall;
- a container lid; and
- a closing/locking mechanism,
- the container lid being arranged on an upper edge of the container trough and lockable with the container trough by the closing/locking mechanism,
- the closing/locking mechanism comprising:
- an actuation lever which is pivotably mounted above the container lid,
- a tension bow directly or indirectly coupled to the actuation lever and displaceable relative to the container lid,
- a spring; and
- an engagement element forming an undercut on the container trough, wherein
- the actuation lever is configured to be pivoted into an actuation position and the tension bow is configured to slide into a sliding position, in which the tension bow moves upwardly toward the upper edge of the container trough and inwardly toward the sidewall of the container trough to engage behind the engagement element and the spring applies a force to the tension bow, thereby pressing the container lid against the container trough, wherein the actuation lever is pivotable relative to the container lid between a locked position, in which the container lid is locked to the container trough in a fluid-tight manner, and an unlocked position, and wherein, when the actuation lever is pivoted from the unlocked position to the locked position: the tension bow engages behind the engagement element, the tension bow moves over the spring and compresses the spring against the container lid, and the spring applies a force to the tension bow, thereby pressing the container trough against the container lid in said fluid-tight manner.

17. The medical sterile container according to claim 16, wherein the tension bow comprises a first section defining a clamping element and a second section defining a locking slider that moves in unison with the clamping element.

18. The medical sterile container according to claim 17, wherein translation of the locking slider is limited by a guide rail on the container lid.

19. The medical sterile container according to claim 17, wherein the engagement element on the container trough comprises an abutment surface, and wherein, when the actuation lever is pivoted from the unlocked position to the locked position, the clamping element contacts the abutment surface on the container trough, and the spring exerts the force on an underside of the tension bow to pull the clamping element against the abutment surface.

20. The medical sterile container according to claim 19, wherein the abutment surface extends along a perimeter of the container trough.

21. The medical sterile container according to claim 19, wherein the abutment surface forms a ledge that extends outwardly and away from an interior of the container trough.

22. The medical sterile container according to claim 19, wherein the clamping element comprises a hook configured to hook onto the abutment surface.

23. The medical sterile container according to claim 22, wherein the hook projects towards the container trough when the container lid is placed on the container trough.

24. The medical sterile container according to claim 19, wherein the spring is arranged between the underside of the tension bow and an upper side of the container lid.

25. The medical sterile container according to claim 16, wherein the actuation lever comprises a first end that forms an actuation handle and a second end that forms a push-down lug, the push-down lug configured to press against the tension bow when the actuation lever is pivoted toward the unlocked position and release the tension bow when the actuation lever is pivoted toward the locked position.

26. The medical sterile container according to claim 16, wherein the spring is a leaf spring that comprises a first free edge and a second free edge, the first free edge and the second free edge configured to engage the tension bow after the actuation lever is pivoted to the locked position and the tension bow slides over the spring.

27. The medical sterile container according to claim 16, wherein the spring is configured such that, when the container trough and the container lid are pressed against each other in said fluid-tight manner, and when a pressure in the medical sterile container exceeds a certain value, said pressure in the medical sterile container overcomes a reaction force of the spring to separate the container lid from the container trough to relieve excess pressure in the medical sterile container.

28. The medical sterile container according to claim 16, wherein the spring is disposed between a portion of the tension bow and a portion of the container lid.

29. The medical sterile container according to claim 16, further comprising a tappet having a first end coupled to the actuation lever and a second end coupled to the tension bow, the tappet being operable to convert pivot motion of the actuation lever to translation of the tension bow.

30. The medical sterile container according to claim 29, wherein the tappet comprises a tappet rod or a tappet plate.

31. The medical sterile container according to claim 16, wherein the actuation lever is pivotally mounted on a pin, and the spring is bent around the pin.

32. A medical sterile container comprising:

a container trough having a sidewall;

a container lid; and a closing/locking mechanism, the container lid being arranged on an upper edge of the container trough and lockable with the container trough by the closing/locking mechanism, the closing/locking mechanism comprising:

an actuation lever which is pivotably mounted above the container lid, a tension bow directly or indirectly coupled to the actuation lever and displaceable relative to the container lid, a spring; and an engagement element forming an undercut on the container trough, wherein:

the actuation lever is configured to be pivoted into an actuation position and the tension bow is configured to slide into a sliding position, in which the tension bow moves upwardly toward the upper edge of the container trough and inwardly toward the sidewall of the container trough to engage behind the engagement element and the spring applies a force to the tension bow, thereby pressing the container lid against the container trough, the actuation lever is pivotable relative to the container lid between a locked position, in which the container lid is locked to the container trough in a fluid-tight manner, and an unlocked position, the tension bow comprises a first section defining a clamping element and a second section defining a locking slider that moves in unison with the clamping element, and translation of the locking slider is limited by a guide rail on the container lid.

* * * * *